United States Patent [19]

Wootton et al.

[11] Patent Number: 4,866,039
[45] Date of Patent: Sep. 12, 1989

[54] PEPTIDES CONTAINING THE 18 TO 23 RESIDUES OF VASOACTIVE INTESTINAL PEPTIDE, AND ANALOGUES

[75] Inventors: Gordon Wootton; Eric A. Watts, both of Harlow; Christine Summers, Sturmer, all of England

[73] Assignee: Beecham Group p.l.c., Middlesex, England

[21] Appl. No.: 920,719

[22] Filed: Oct. 17, 1986

[30] Foreign Application Priority Data

Oct. 19, 1985 [GB] United Kingdom ............... 8525852

[51] Int. Cl.[4] ..................... A61K 37/02; C07K 7/06
[52] U.S. Cl. ........................... 514/16; 514/17; 514/925; 530/328; 530/329
[58] Field of Search ............... 530/328, 329; 514/16, 514/17

[56] References Cited

U.S. PATENT DOCUMENTS 4,237,046 12/1980 Bodanszky ..................... 530/329

FOREIGN PATENT DOCUMENTS 0184309 6/1986 European Pat. Off. .

OTHER PUBLICATIONS

Lehninger et al. Biochemistry, Worth Publishers, Inc., pp. 71–75 (New York, 1975).

Rudinger, Peptide Hormone, Parsons (ed)., U. Park Press, Baltimore (1976).
Robberecht et al., Gut Hormones, 101, pp. 97–103 (1978).
Chemical Abstracts, vol. 102, 1985, p. 65, abstract No. 675y.
Chemical Abstracts, vol. 100, 1984, p. 675, abstract No. 175257z.
A. Couvineau et al., "Structural Requirements For VIP Interaction With Specific Receptors in Human and Rat Intestinal Membranes: Effect of Nine Partial Sequences," *Biochemical and Biophysical Research Communications*, 121, pp. 493–498 (1984).
M. Bodanszky et al., "A Preferred Conformation in the Vasoactive Intestinal Peptide (VIP), Molecular Architecture of Gastrointestinal Hormones," *Bioorganic Chemistry*, 3, pp. 133–140 (1974).

*Primary Examiner*—Delbert R. Phillips
*Assistant Examiner*—Christina Chan
*Attorney, Agent, or Firm*—James F. Haley, Jr.; David K. Barr; Doreen F. Shulman

[57] ABSTRACT

Peptides comprising, in sequence, units selected from the amino acid residues 17 to 24 of VIP, and consisting at least of the amino acid residues 18 to 23, or an analogue thereof wherein one or more of the amino acid residues is replaced by an equivalent other amino acid; having anti-ulcer activity, a process for their preparation and their use as pharmaceuticals.

12 Claims, No Drawings

PEPTIDES CONTAINING THE 18 TO 23 RESIDUES OF VASOACTIVE INTESTINAL PEPTIDE, AND ANALOGUES

The invention relates to VIP fragments and analogues, processes for their preparation, pharmaceutical preparations containing them and their use in medicine.

Vasoactive intestinal peptide (VIP) was originally isolated from the small intestines of the hog, but it has since been isolated from other species, such as the chicken, and has been shown to have a wide distribution throughout body tissues.

It has systemic vasodilator activity. It induces systemic hypotension and increases cardiac output on intravenous infusion. It increases hepatic arterial blood flow, increases blood sugar levels, and has the ability to bring about tracheal relaxation, and relaxation of gut smooth muscle, as well as stimulation of the output of bicarbonate from intestinal secretions. It therefore appears to be useful in treatment of hypertension and peripheral vascular disease on parenteral administration, and as a bronchodilator on aerosol or parenteral administration.

Vasoactive intestinal peptide comprises a peptide having a sequence of 28 amino acids in a single chain. The sequence of VIP (pig) is shown in table 1.

Abbreviations used are as follows:

| Amino Acid Residue | Abbreviations |
|---|---|
| alanine | Ala |
| arginine | Arg |
| asparagine | Asn |
| aspartic acid | Asp |
| glutamine | Gln |
| histidine | His |
| isoleucine | Ile |
| leucine | Leu |
| lysine | Lys |
| methionine | Met |
| norleucine | Nle |
| phenylalanine | Phe |
| serine | Ser |
| threonine | Thr |
| tyrosine | Tyr |
| valine | Val |

The amino acid components are in the L-form.

VIP (chicken) is closely related, differing in the 11, 13, 26 and 28 position; the peptide has:

| a serine residue | in position 11, |
|---|---|
| a phenylalanine residue | in position 13, |
| a valine residue | in position 26 and |

TABLE 1

VIP (pig)

N-Terminus

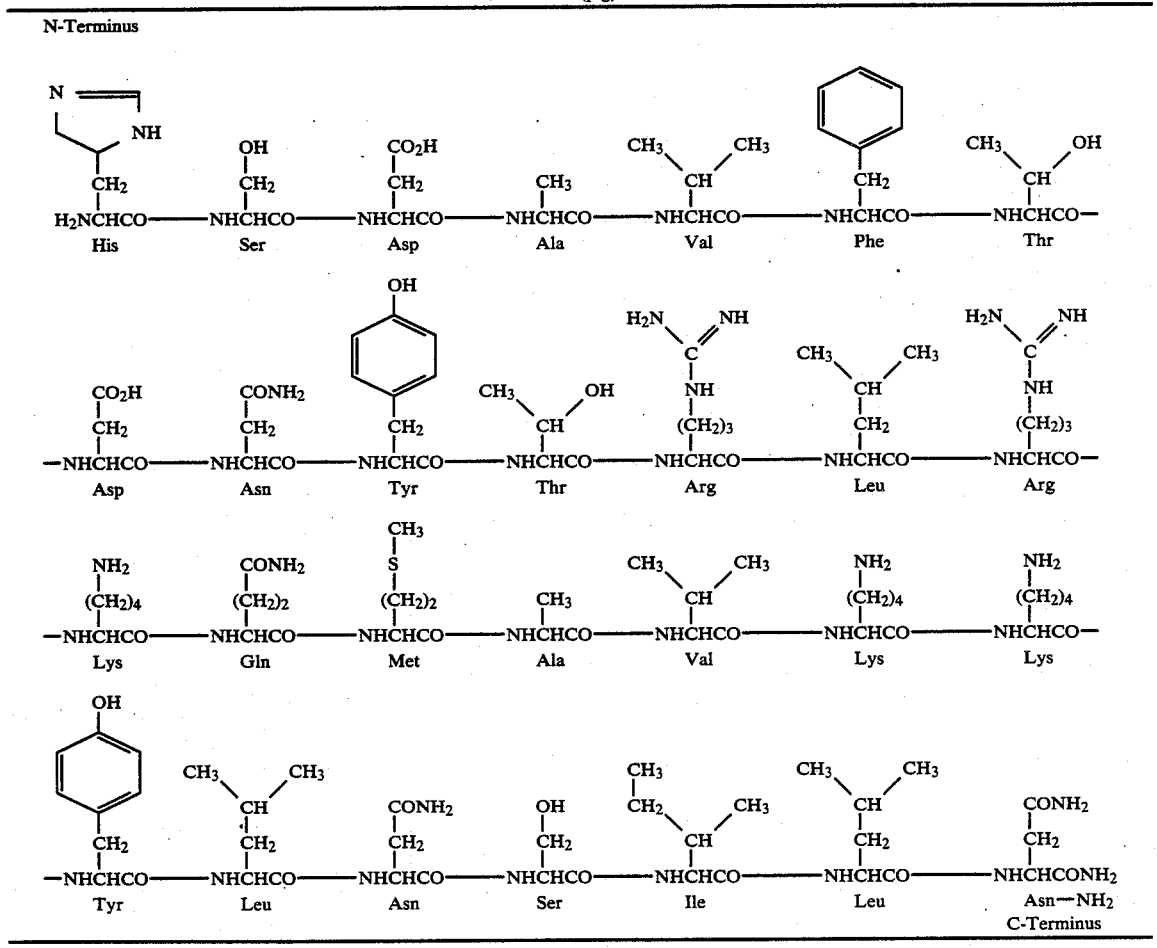

C-Terminus

| a threonine residue | in position 28. |

A number of C-terminal fragments have been produced, mostly in the synthetic programme required to prove the structure of VIP. Few structures have been obtained from the N-terminus, and very little work has been carried out on fragments from the centre of the molecule.

It has, however, been concluded (Robberecht, Gut Hormones (1978) edited by Bloom, p 97 to 103) that the C-terminus of VIP holds the receptor recognition site, and that the N-terminus holds the activation site, together with a minimal capacity for binding.

Counter to the commonly held views regarding the activity of VIP, we have found that there is pharmacological activity even in the absence of the amino acid units at the C- and N-termini of the molecule.

The present invention provides a peptide comprising, in sequence, units selected from the amino acid residues 17 to 24 of VIP, and consisting at least of the amino acid residues 18 to 23, or an analogue thereof wherein one or more of the amino acid residues is replaced by an equivalent other amino acid.

The present invention also provides a peptide or an analogue thereof as described above, having pharmacological activity.

Preferably in a peptide of the present invention, the amino acid units are those of 18 to 23 of VIP, or an analogue thereof.

In an analogue thereof, one or more than one amino acid unit may be replaced by an equivalent amino acid unit.

Amino acids can be considered as members of different classes; such groupings are well known. Replacement of an amino acid of the peptide by an equivalent amino acid may be by another amino acid of the same class, and where an amino acid can be grouped into two or more classes, replacement may be made from one or more of these classes.

All amino acids in an analogue of the present invention may, for example, be naturally occurring amino acids, i.e. L-amino acids, or amino acids in the D- or DL-form.

It seems reasonable to suppose that the activity of a peptide bears some relationship to its secondary structure (which could be inherent, or adopted at the receptor site). Thus the expressed activity could be related to a potential for formation of a highly ordered arrangement of some of the amino acids.

Where there is replacement of one or more amino acids, the replacement may, for example, be such that the essential structure of the fragment is maintained.

Thus, for example:

the methionine at position 17 may, if desired, be replaced by another neutral amino acid, e.g. the isosteric norleucine (Nle) or leucine (Leu);

the alanine at position 18 may, if desired, be replaced by another hydrophobic amino acid, e.g. glycine (Gly) or norvaline (Nva);

the valine at position 19 may, if desired, be replaced by another hydrophobic amino acid, e.g. leucine (Leu);

the tyrosine at position 22 may, if desired, be replaced by another hydrophobic amino acid, especially an aromatic amino acid, e.g. phenylalanine (Phe).

the leucine at position 23 of VIP (pig) may, if desired, be replaced by another hydrophobic amino acid, e.g. valine (Val);

the asparagine at position 24 may if desired be replaced by another carboxamido amino acid, e.g. glutamine (Gln).

Especially, there should be mentioned analogues in which one or more of the amino acid residues 17 to 24 is replaced by an equivalent other amino acid and any additional amino acid residues present correspond to those in VIP.

Very especially, the present invention provides the hexapeptide

Ala Y Lys Lys Tyr Leu where Y represents Val or Ala.

Fragments and analogues of VIP (pig) should especially be mentioned, but the basic structure may correspond to VIP from any source.

The amino acids may, for example, be in the L-form; although one or more D-amino acids may, if desired, be present in the structure.

The carboxy terminus of the peptides or analogues of the present invention may be in the form of the acid (—OH); an ester, for example an alkyl ester, especially a ($C_1$–$C_4$)-alkyl ester, e.g. the methyl ester, (—OCH$_3$), the hydrazine (—NH—NH$_2$), or an amide, usually the unsubstituted amide (—NH$_2$). Preferably the carboxy-terminus is in the form of the unsubstituted amide.

The amino-terminus of the peptides or analogues of the present invention may be in the form of the unsubstituted amine (—NH$_2$) or protected amine (—NHR) where R represents, for example, acetyl, tert.-butyloxycarbonyl or benzyloxycarbonyl, or in the form of an acid addition salt, preferably a physiologically tolerable, pharmaceutically acceptable acid addition salt, of the amine.

Acid addition salts may be, for example, salts with inorganic acids such, for example, as hydrochloric acid, hydrobromic acid, orthophosphoric acid or sulphuric acid, or organic acids such, for example, as methanesulphonic acid, toluenesulphonic acid, acetic acid, trifluoroacetic acid, propionic acid, lactic acid, citric acid, tartaric acid, fumaric acid, malic acid, succinic acid, salicylic acid or acetylsalicylic acid.

Thus, more particularly, the present invention provides a polypeptide of the general formula $$X-Y_n-Y_{18}Y_{19}Y_{20}Y_{21}Y_{22}Y_{23}-Y_m-Z \qquad \text{I}$$

in which

X represents a hydrogen atom or an amine-protecting group, preferably a hydrogen atom;

$Y_n$ represents a direct bond or $Y_{17}$ wherein $Y_{17}$ represents Met or the residue of another neutral amino acid, $Y_{18}$ represents Ala or the residue of another hydrophobic amino acid, $Y_{19}$ represents Val or the residue of another hydrophobic amino acid, $Y_{20}$ represents Lys or the residue of another basic amino acid, $Y_{21}$ represents Lys or the residue of another basic amino acid, $Y_{22}$ represents Tyr or the residue of another hydrophobic amino acid, $Y_{23}$ represents Leu or the residue of another hydrophobic amino acid;

Ym represents a direct bond or Y24 wherein Y24 represents asparagine or another carboxamido amion acid, and Z represents a hydroxyl group, or a group of the formula OR such that COZ represents an ester, or a hydrazino group such that COZ represents a hydrazide, or NH2 such that COZ represents an amide, preferably NH2; and salts thereof, preferably physiologically tolerable salts thereof, especially physiologically tolerable acid addition salts thereof.

The compounds of formula I are preferably in pharmaceutically acceptable form. By pharmaceutically acceptable form is meant, inter alia, of a pharmaceutically acceptable level of purity excluding normal pharmaceutical additives such as diluents and carriers, and including no material considered toxic at normal dosage levels. A pharmaceutically acceptable level of purity will generally be at least 50% excluding normal pharmaceutical additives, preferably 75%, more preferably 90% and still more preferably 95%.

A peptide or analogue of the invention may be prepared by those methods known in the art for the synthesis of compounds of analogous structure and in this regard reference is made, by way of illumination only, to the following literature;

(a) Y.S. Klausner and M.Bodanszky, *Bioorg. Chem.* (1973), 2, p 354–362.

(b) M. Bodanszky, C.Yang Lin and S.I.Said, *Bioorg. Chem.* (1974), 3, p 320–323.

(c) S.R. Pettit, "*Synthetic Peptides*", (Elsevier Scientific Publishing Co. 1976).

(d) Stewart and Young, "*Solid Phase Peptide Synthesis*" (W.H.Freeman and Co. 1969).

(e) E.Atherton, C.J. Logan and R.C.Sheppard, *J.C.S. Perkin I*, (1981) p 538–546.

(f) E.Brown, R.C. Sheppard and B.J. Williams, J.C.S. Perkin I, (1983) p 1161–1167.

The present invention also provides a peptide or analogue of the present invention which has been prepared synthetically.

A peptide or analogue of the present invention may, for example, be formed by the sequential coupling of appropriate amino acids or by the initial preparation and subsequent coupling of peptide subunits, themselves prepared in stepwise manner; in either case either classical solution chemistry methods of peptide synthesis or solid phase procedures may be used.

The coupling reactions may be effected by, for example, activating the reacting carboxyl group of the ingoing amino acid, and reacting this with the amino group of the substrate unit. Details of suitable, optional activating and protecting (masking) groups and of suitable reaction conditions (for the coupling reactions and for the introduction and removal of protecting groups) giving, preferably, the minimum of racemisation, may be found in the above-referenced literature.

Accordingly, the present invention further provides a process for the preparation of a peptide or analogue of the present invention, which comprises coupling a suitable amino acid or amino acid sequence in which the carboxyl group is activated with an appropriate amino acid or amino acid sequence and repeating, if necessary, the coupling procedure until there is obtained a peptide comprising, in sequence, units of the amino acid residues 17 to 24 of VIP consisting at least of the amino acid residues 18 to 23, or an analogue thereof in which one or more of the amino acid residues is replaced by an equivalent other amino acid, wherein, if desired or required, non-reacting functional groups are protected during the coupling procedure and, if desired, subsequently deprotected.

A polypeptide of the general formula I may thus be prepared by reacting a reagent of the general formula

$$H—Y^1—OH \qquad (II)$$

wherein $Y^1$ represents an amino acid unit or a partial radical sequence identical with the corresponding N-terminal amino acid unit or partial radical sequence in formula I, with a reagent of the general formula

$$H—Y^2—OH \qquad (III)$$

wherein $Y^2$ represents an amino acid unit or a partial radical sequence identical with that in the balance of the above-defined product peptide, the reagents (II) and (III) being optionally protected and/or activated where and as appropriate, followed if desired or required by one or more of the following:

deprotection of the products, conversion of one carboxy terminus into another carboxy terminus, conversion of a free peptide into a salt thereof.

For example, an appropriate peptide ester of the general formula

$$X—Y^1—Y^2—OR \qquad (IV)$$

wherein X, $Y^1$ and $Y^2$ have the meanings given above and R represents, for example, an alkyl group and preferably an alkyl group having 1 to 4 carbon atoms, may be converted into an amide by reaction with ammonia.

Compounds of the general formulae II, III and IV may themselves be prepared by standard techniques analogous to those described above.

It will be appreciated that protected forms of a peptide or analogue of the present invention are useful novel intermediates and form an aspect of the invention.

A peptide or analogue of the present invention may also be prepared on a solid phase support, for example, a polyamide or a polystyrene resin, using amino acids protected at the N-terminus, for example, with the fluorenylmethyloxycarbonyl group or the t-butyloxycarbonyl group and with appropriate protection of any side-chain functional groups.

One such reaction scheme for solid-phase peptide synthesis is, for example, illustrated below.

Solid Phase Scheme

A.A.  = Amino acid
t-BOC = t- Butyloxy-
         carbonyl
Fmoc  = Fluorenyl-
         methyloxy-
         carbonyl,
         i.e.

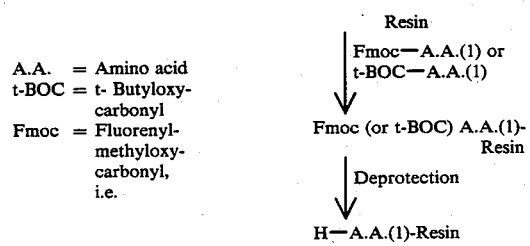

-continued

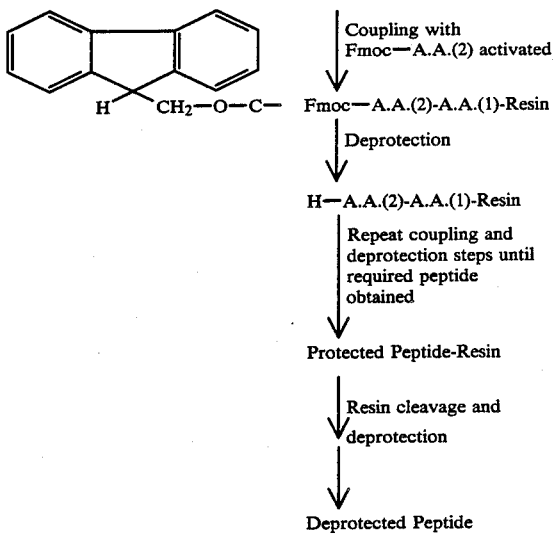

Coupling with
Fmoc—A.A.(2) activated

↓

Fmoc—A.A.(2)-A.A.(1)-Resin

↓ Deprotection

H—A.A.(2)-A.A.(1)-Resin

↓ Repeat coupling and
deprotection steps until
required peptide
obtained

Protected Peptide-Resin

↓ Resin cleavage and
deprotection

Deprotected Peptide

This technique involves the addition of the first protected amino acid to a solid resin support. After removal of the protecting group (deprotection) the amino acid-resin is coupled with the next protected amino acid in its activated form. The deprotection/coupling procedures are repeated until the required peptide is obtained. The peptide is then cleaved from the resin before final removal of the protecting groups. Alternatively, when desired or necessary, the protecting groups may be removed before cleavage of the peptide from the resin.

Advantageously the Fmoc group is the form of protection used for the α-amino function of the amino acids involved (but not for side chain protection).

However, the last amino acid in each synthesis is generally protected as its t-BOC or Fmoc derivative. This allows the peptide to remain fully protected on cleavage from the resin.

The use of alternative resins may also require the need for removal of protecting groups prior to resin cleavage. In this case it is likely that the Fmoc-protecting group would be used for Nα protection throughout the syntheses.

The peptides and analogues of the present invention have anti-ulcer activity and they may be a useful new approach to duodenal ulcer therapy.

The present invention further provides a peptide or analogue of the present invention, for use in a method of treatment of the human or animal body.

Where the fragment or analogue is in the form of a salt thereof, it should of course be understood that this is a physiologically tolerable salt, which is pharmaceutically acceptable.

The peptide or analogue of the invention may be administered per se or, preferably, as a pharmaceutical composition also including a pharmaceutically acceptable carrier.

Accordingly, the present invention provides a pharmaceutical composition, which comprises a peptide or analogue of the present invention, in admixture or conjunction with a pharmaceutically acceptable carrier.

The preparation may, if desired, be in the form of a pack accompanied by written or printed instructions for use.

In accordance with conventional pharmaceutical practice the carrier may comprise a diluent, filler, disintegrant, wetting agent, lubricant, colourant, flavourant or other conventional additive.

Preferably, a pharmaceutical composition of the invention is in unit dosage form.

The suitable dosage range for compounds of the invention may vary from compound to compound and may depend on the condition to be treated. It will also depend, inter alia, on the relation of potency to absorbability and on the mode of administration chosen.

Suitable formulations are, for example, intravenous infusions, aerosols and enteric coated capsules.

The present invention further provides a method of treatment of mammals, including humans, which comprises administering an effective, non-toxic, amount of a peptide or analogue of the present invention to the mammal; and a peptide or analogue of the present invention for use as a pharmaceutical, in particular for the treatment of peptic ulcers.

Conveniently, the active ingredient may be administered as a pharmaceutical composition hereinbefore defined, and this forms a particular aspect of the present invention.

A suitable dose is, for example, in the range of from 1 to 2.5 mg/kg i.v. in the rat. A possible daily dose for humans is, for example, 0.01 to 50 mg by intravenous infusion, 0.01 to 250mg by aerosol or 0.1 to 500 mg by enteric coated capsule.

No adverse toxicological effects are indicated at the aforementioned dosage ranges.

In the following, the various derivatives protecting groups, reagents and solvents are referred to by abbreviations for convenience.

| Abbreviation | Group/Reagent etc. |
| --- | --- |
| BOC | t-Butyloxycarbonyl |
| Fmoc | Fluorenylmethyloxycarbonyl |
| DMF | Dimethylformamide |
| DCC | Dicyclohexylcarbodiimide |
| HOBT | 1-Hydroxybenzotriazole |
| DCU | Dicyclohexylurea |
| PITC | Phenylisothiocyanate |

Solid Phase Synthesized Peptides (a) The following examples were synthesized by solid phase methods using the 4-hydroxymethylbenzoylnorleucyl derivatised polydimethylacrylamide gel resin Pepsyn B (1.0mequiv/g or 0.3mequiv/g) as supplied by Cambridge Research Biochemicals Ltd.

DMF was fractionally distilled in vacuo from ninhydrin before use and stored over pre-activated molecular sieves (4A). Piperidine was freshly distilled from a suitable drying agent. Dichloromethane (A.R) was dried over pre-activated molecular sieves (4A).

The amino acids were chosen as their Fmoc-derivatives with BOC— or t—Bu— side chain protection where necessary.

The symmetrical anhydride of the first amino acid (2.5equiv), (prepared as described by E. Brown et al in J.C.S. Perkin I, 1983, 80) was added to the resin (1 equiv) in DMF (10-15ml) in the presence of a catalytic quantity of dimethylaminopyridine. The mixture was agitated with $N_2$ and the reaction was allowed to proceed for 1h. The resin was drained and the addition procedure was repeated. The drained resin was then washed with DMF (10-15ml ×1 min ×10).

The removal of the Fmoc protecting groups was achieved by agitation of the peptide-resin with piperidine (10ml; 20% in DMF) for 3 min then 7 min.

Subsequent addition of each amino acid was carried out using the Fmoc symmetrical amino acid anhydrides (2.5 equiv) or the preformed hydroxybenzotriazole ester (3.0 equiv) (from Fmoc-amino acid, DCC and HOBT).

Amino acids containing amidic side chains (e.g Gln or Asn) were coupled as their p-nitrophenyl activated esters (3.0equiv) in the presence of hydroxybenzotriazole (6.0equiv). Alternatively, the protected amino acid can be coupled in the presence of DCC and HOBt in situ.

Fmoc-Arginine was coupled to the peptide resin via its hydroxybenzotriazole ester. This was prepared by suspending Fmoc-Arginine (10equiv) in DMF (10ml) and adding HOBT (30 equiv). The clear solution was added to the resin and agitated for 1 minute. DCC (10 equiv) was then added and the reaction was allowed to proceed to completion.

The final amido acid in the chosen sequence was added as its $N\alpha$ Boc derivative either as the symmetrical anhydride or as the preformed hydroxybenzotriazole ester.

Boc-Arginine was coupled as its hydrochloride and activated by addition of DCC (5 equiv) to the protected hydrochloride salt (10 equiv) in DMF (10–15ml) 5 minutes prior to addition of the whole reaction mixture to the peptide-resin (1 equiv).

In some cases, Fmoc-amino acid anhydrides (eg Phe, Ala, Gly) coprecipitated with DCU during their formation. In these cases, the anhydrides were prepared in the presence of 10% DMF in dichloromethane. Dichloromethane was removed in vacuo before addition of the whole mixture to the peptide resin. Couplings in general were carried out for 1–2h and repeated if necessary. Completeness of acylation was verified by a qualitative Kaiser ninhydrin test as described by E. Kaiser et al in Anal. Biochem. (1970) p.34.

Peptide cleavage from the resin was accomplished via ammonolysis to provide the protected peptide amine. To this end, when the final coupling was complete, the peptide-resin was washed with DMF (10–15ml ×1 min ×10), anhydrous dichloromethane (10–15ml ×1 min ×10) and dry ether (10ml ×1 min ×10). The collapsed resin was dried over silica gel for 1 hour in a vacuum dessicator. The resin was re-swollen as previously described, drained and treated with a saturated solution of ammonia in methanol at $-10°$. The vessel was sealed and allowed to reach ambient temperatures for 2 days. The apparatus was cooled, opened and the contents were allowed to warm to room temperature. The suspension was filtered under suction and the resulting residue was washed with methanol (5 ×5ml) and DMF (5 ×5ml). The combined washings and filtrate were evaporated in vacuo. The resulting residue was triturated with dry ether and filtered to give the protected peptide.

The final acidolytic deprotection procedure removes all protecting groups (e.g. BOC, t-Bu) from the peptide amide. Thus the protected peptide was dissolved in trifluoroacetic acid (4ml/100mg of peptide) and stirred at room temperature for 3h. In some cases, hydrogen bromide gas was bubbled through the mixture during this time. The mixture was evaporated in vacuo and the resulting solid was triturated with dry ether (7 ×5ml) to give the required peptide ether as its trifluoroacetate or its hydrobromide salt. The peptides were purified by one or a combination of methods listed below.

(a) Conversion to acetate salt.

The peptide salt was dissolved in a minimum amount of water and passed down a strong anion exchange resin which was in its acetate form (e.g. Sephadex QAE-A-25). Eluant was fractionated and the fractions containing desired materials were lyophilised.

(b) Selective adsorption chromatography

The peptide salt was dissolved in a minimum amount of water and adsorbed onto a weak cation exchange resin (e.g. Sephadex CM-25). The peptide acetate was recovered during elution with an increasing concentration of $NH_4OAc$ (0.05M –0.5M) at pH 7, an increasing pH gradient (pH 7 –pH 9) or a combination of both.

(c) High Performance Liquid Chromatography.HPLC

The peptide was purified by preparative HPLC on reverse phase $C_{18}$ silica columns (e.g. μbondapak, Hypersil ODS).

The peptides were characterised by 24h acidolytic cleavage and PITC derivatised amino acid analysis (Waters Picotag system) and fast atom bombardment (FAB) mass spectrometry (Jeol DX 303).

EXAMPLE 1

H-Ala-Val-Lys-Lys-Tyr-Leu-NH$_2$ (El)

(El) was prepared using the 1.0 mequiv./g Pepsyn B resin. [MH]$^+$(F.A.B.) =720. Amino acid analysis; Ala (0.9), Val (0.7), Leu (0.9), Tyr (0.9), Lys (1.8).

EXAMPLE 2 H-Ala-Ala-Lys-Lys-Tyr-Leu-NH$_2$ (E2)

(E2) was prepared using the 1.0 mequiv./g Pepsyn B resin. [MH]$^+$(F.A.B.) =692. Amino acid analysis; Ala (2.1), Leu (1.1), Tyr (1.1), Lys (2.1).

EXAMPLE 3 H-Ala-Leu-Lys-Lys-Tyr-Leu-NH$_2$ (E3)

(E3) was prepared using the 1.0 mequiv./g Pepsyn B resin. [MH]$^+$(F.A.B.) =734.

Pharmacological Data

Anti-ulcer Activity

Anti-ulcer activity may be related to the enhanced capacity to dispose of gastric acid. Acid disposal capacity may be enhanced by increased intestinal secretions, and enhanced acid disposal capacity is believed to be useful in the treatment of peptic ulcer disease.

Method for estimating the acid disposal capacity of the rat proximal duodenum Male Wistar rats, 180–250g bodyweight, fasted overnight, are anaesthetized with urethane (150mg/100g bodyweight i.m.). The trachea is cannulated, and a gastric cannula, 0.5cm i.d., 3cm long, is inserted into the non-glandular forestomach via a mid-line abdominal incision. The intragastric cannula is exteriorized via a stab wound in the body wall. A triple lumen catheter, 0.3cm o.d., is passed via the gastric cannula through the pylorus. The duodenum is ligated 1cm below the pylorus, and the pylorus ligated around the cannula, thus creating a 1cm proximal duodenal pouch excluding pancreatic and biliary secretions. The two ligatures enclosing the duodenal pouch are placed so as to avoid occluding the blood supply to the duodenal segment. Gastric secretions are allowed to drain freely from the gastric cannula. Compounds are administered dissolved in 0.9% sodium chloride (saline) as a 1.2 ml/h infusion via a catheter inserted in a jugular vein.

The triple lumen catheter is connected as follows. Lumen 1 delivers perfusing medium at 0.1ml/min via a peristaltic pump.

Lumen 2 collects the perfusate and delivers it to a flow cell containing a pH microelectrode. Outflow pH is recorded throughout the experiment. Lumen 3 is connected to a pressure transducer to monitor intraluminal pouch pressure. Body temperature is maintained at 34° C. throughout the experiments.

After preparation, the duodenal segment is perfused with saline, adjusted to pH 6.5 with hydrochloric acid, for 30 minutes. The perfusing medium is then changed successively to saline adjusted with hydrochloric acid to pH 4, 3.5, 3 and 2.5 in increasing order of acidity. Each solution is perfused for 40 minutes. At the end of the pH 2.5 infusion period, saline pH 6.5 is perfused for 30 minutes, and the descending pH series repeated. This procedure produces two series of input pH/output pH values, designated 1st and 2nd passes.

A group size of 6 animals or larger is used and the effect of compounds on the output pH compared to control data determined. For comparisons between groups, Student's 't' test is used. Significance is taken at $P<0.05$.

The compound of example I caused a significant increase in acid disposal at input pH 2.5 on the second pass at a dose of 150nmol/kg/h.

We claim:

1. A polypeptide of the general formula

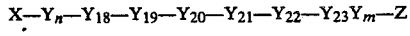

$$X-Y_n-Y_{18}-Y_{19}-Y_{20}-Y_{21}-Y_{22}-Y_{23}Y_m-Z \quad I$$

in which
X represents a hydrogen atom or an amine-protecting group;
$Y_n$ represents a direct bond or $Y_{17}$ wherein
$Y_{17}$ represents Met or the residue of another naturally occurring neutral amino acid,
$Y_{18}$ represents Ala or the residue of another naturally occurring hydrophobic amino acid,
$Y_{19}$ represents Val or the residue of another naturally occurring hydrophobic amino acid,
$Y_{20}$ represents Lys or the residue of another naturally occurring basic amino acid,
$Y_{21}$ represents Lys or the residue of another naturally occurring basic amino acid,
$Y_{22}$ represents Tyr or the residue of another naturally occurring hydrophobic amino acid,
$Y_{23}$ represents Leu or the residue of another naturally occurring hydrophobic amino acid;
$Y_m$ represents a direct bond or $Y_{24}$ wherein $Y_{24}$ represents asparagine or another naturally occurring carboxamido amino acid, and
Z represents a hydroxyl group, or a group of the formula OR such that COZ represents an ester, or a hydrazino group such that COZ represents a hydrazide, or $NH_2$ such that COZ represents an amide; and pharmaceutically acceptable salts thereof.

2. A polypeptide according to claim 7 wherein $Y_n$ is a direct bond and $Y_m$ is a direct bond.

3. A polypeptide according to claim 7 wherein all the amino acids are in the L-form.

4. A polypeptide according to claim 7 in which one or more of the amino acid residues $Y_{10}$ to $Y_{23}$ is replaced by an equivalent other amino acid, as defined in claim 7, and additional amino acid residues present correspond to those in $Y_{17}$ or $Y_{24}$, when present, are methionine and asparagine, respectively.

5. A polypeptide according to claim 1 wherein the carboxy-terminus of the polypeptide is in the form of the unsubstituted amide.

6. A polypeptide according to claim 1 wherein the amino-terminus of polypeptide is in the form of the unsubstituted amine.

7. The hexapeptide
Ala Y Lys Lys Tyr Leu
wherein Y represents Val or Ala.

8. H—Ala—Val—Lys—Lys—Tyr—Leu—$NH_2$.
9. H—Ala—Ala—Lys—Lys—Tyr—Leu—$NH_2$.
10. H—Ala—Leu—Lys—Lys—Tyr—Leu—$NH_2$.

11. An anti-ulcer pharmaceutical composition comprising an effective amount of a polypeptide according to claim 1, and a pharmaceutically acceptable carrier.

12. A method of treatment of ulcers in mammals which comprises the administration of an effective amount of a polypeptide according to claim 1.